(12) United States Patent
Khan

(10) Patent No.: US 12,016,940 B2
(45) Date of Patent: Jun. 25, 2024

(54) DENTIFRICE COMPRISING A PVM-MA COPOLYMER AND A SOURCE OF FREE FLUORIDE IONS

(71) Applicant: GlaxoSmithKline Consumer Healthcare (UK) IP Limited, Middlesex (GB)

(72) Inventor: Shazada Yassar Khan, Surrey (GB)

(73) Assignee: HALEON UK IP LIMITED, Middlesex (GB)

( * ) Notice: Subject to any disclaimer, the term of this patent is extended or adjusted under 35 U.S.C. 154(b) by 108 days.

(21) Appl. No.: 17/252,393

(22) PCT Filed: Jul. 3, 2019

(86) PCT No.: PCT/EP2019/067790
§ 371 (c)(1),
(2) Date: Dec. 15, 2020

(87) PCT Pub. No.: WO2020/007887
PCT Pub. Date: Jan. 9, 2020

(65) Prior Publication Data
US 2021/0259932 A1  Aug. 26, 2021

(30) Foreign Application Priority Data
Jul. 5, 2018 (GB) ..................... 1811065

(51) Int. Cl.
| A61Q 11/00 | (2006.01) |
| A61K 6/00 | (2020.01) |
| A61K 8/19 | (2006.01) |
| A61K 8/21 | (2006.01) |
| A61K 8/362 | (2006.01) |
| A61K 8/81 | (2006.01) |

(52) U.S. Cl.
CPC .............. *A61K 8/21* (2013.01); *A61K 8/19* (2013.01); *A61K 8/362* (2013.01); *A61K 8/8129* (2013.01); *A61Q 11/00* (2013.01)

(58) Field of Classification Search
CPC ........ A61Q 11/00; A61Q 17/005; A61K 8/21; A61K 8/8147; A61K 2800/92; A61K 6/00; A61K 8/8164; A61K 8/8141; A61K 8/0216; A61K 8/69
See application file for complete search history.

(56) References Cited

U.S. PATENT DOCUMENTS

| 4,137,303 A | * | 1/1979 | Gaffar ................. A61K 8/416 |
| | | | 424/52 |
| 4,627,977 A | | 12/1986 | Gaffar et al. |
| 4,775,523 A | | 10/1988 | Sparacio et al. |
| 4,889,712 A | | 12/1989 | Gaffar et al. |
| 5,000,944 A | | 3/1991 | Prencipe et al. |
| 5,156,835 A | | 10/1992 | Nabi et al. |
| 5,188,821 A | * | 2/1993 | Gaffar ..................... A61K 8/24 |
| | | | 106/35 |
| 5,202,112 A | | 4/1993 | Prencipe et al. |
| 5,240,697 A | | 8/1993 | Norfleet et al. |
| 5,690,911 A | | 11/1997 | Mirajkar et al. |
| 2003/0157033 A1 | * | 8/2003 | Endo ..................... A61K 8/347 |
| | | | 424/49 |
| 2003/0180229 A1 | * | 9/2003 | Kosti ..................... A61K 8/42 |
| | | | 424/53 |
| 2006/0022634 A1 | * | 2/2006 | Nomura ................ H01M 50/24 |
| | | | 320/107 |
| 2006/0140879 A1 | | 6/2006 | Fruge et al. |
| 2008/0152599 A1 | * | 6/2008 | Brignoli .............. A61K 8/8164 |
| | | | 424/49 |
| 2009/0087501 A1 | * | 4/2009 | Cummins .............. A61K 36/15 |
| | | | 424/754 |
| 2009/0202450 A1 | | 8/2009 | Prencipe et al. |
| 2009/0238777 A1 | * | 9/2009 | Joziak ..................... A61P 1/02 |
| | | | 424/52 |
| 2011/0020248 A1 | | 1/2011 | Strand |
| 2012/0288455 A1 | | 11/2012 | Pilch et al. |
| 2013/0230469 A1 | | 9/2013 | Lewus et al. |
| 2016/0324741 A1 | | 11/2016 | Baig et al. |

FOREIGN PATENT DOCUMENTS

WO    WO 02/45678 A2    6/2002

OTHER PUBLICATIONS

Wang et al.: "Fluoride release and anti-erosive effects of dentifrices containing PVM-MA copolymers", Journal of Dentistry, vol. 41, 2013, —2013, pp. 148-154, XP002795040, paragraph [02.2]; table 1.
Luis Eduardo Silva Soares et al: "Micro Energy-Dispersive X-Ray Fluoresence Mapping of Enamel and Dental Materials after Chemical Erosion", Microscopy and Microanalysis, vol. 18, No. 5, Oct. 1, 2012 (Oct. 1, 2012), pp. 1112-1117, XP001578811, ISSN: 1431-9276, DOI: 10.1017/S1431927612001535 [retrieved on Oct. 25, 2012] abstract table 1 paragraph [conclusions].
Nuran Nabi et al: "In vitro and in vivo studies on triclosan/PVM/MA copolymer/NaF combination as an anti-plaque agent", American Journal of Dentistry, vol. 2, Sep. 1, 1989 (Sep. 1, 1989), pp. 197-206, XP001628654, abstract.
Anonymous: "Imagine a healthy beautiful smile", Jan. 1, 2017 (Jan. 1, 2017), XP055633000, Retrieved from the Internet: URL:https://www.ashland.com/file_source/Ashland/links/PHC17 1004 OralCare US112217.pdf [retrieved on Oct. 16, 2019] pp. 6,7.

(Continued)

*Primary Examiner* — Tracy Liu

(57) ABSTRACT

A dentifrice composition is described comprising a source of free fluoride ions; and from 0.1% to less than 0.5% by weight of the composition of a copolymer of methyl vinyl ether with maleic anhydride or acid; and wherein the composition has a slurry pH from 6.0 to 7.5, and wherein the composition is free of a carboxylic acid or alkali metal salt thereof wherein the acid is selected from the group consisting of malonic acid, glutaric acid, tartaric acid, lactic acid and mixtures thereof. The composition enhances fluoride uptake into teeth and provides protection against acidic challenges.

8 Claims, 3 Drawing Sheets

(56) References Cited

OTHER PUBLICATIONS

Database GNPD [Online] MINTEL; Feb. 5, 2018 (Feb. 5, 2018), anonymous: "CC Care Correction Bright Whitening Toothpaste", XP055552590, retrieved from www.gnpd.com Database accession No. 5429007 paragraph [ingredients].

Database GNPD [Online] MINTEL; Jul. 7, 2016 (Jul. 7, 2016), anonymous: "Fresh Mint Toothpaste", XP055631334, retrieved from www.gnpd.com Database accession No. 4127829 paragraph [ingredients].

Database GNPD [Online] MINTEL; May 15, 2018 (May 15, 2018), anonymous: "Anti-Cavity Toothpaste with Fluoride", XP055631330, retrieved from www.gnpd.com Database accession No. 5668227 paragraph [ingredients].

* cited by examiner

Figure 1: Effect of PVM/MA (pH 6.2) on EFU (mean, ± s.e.)
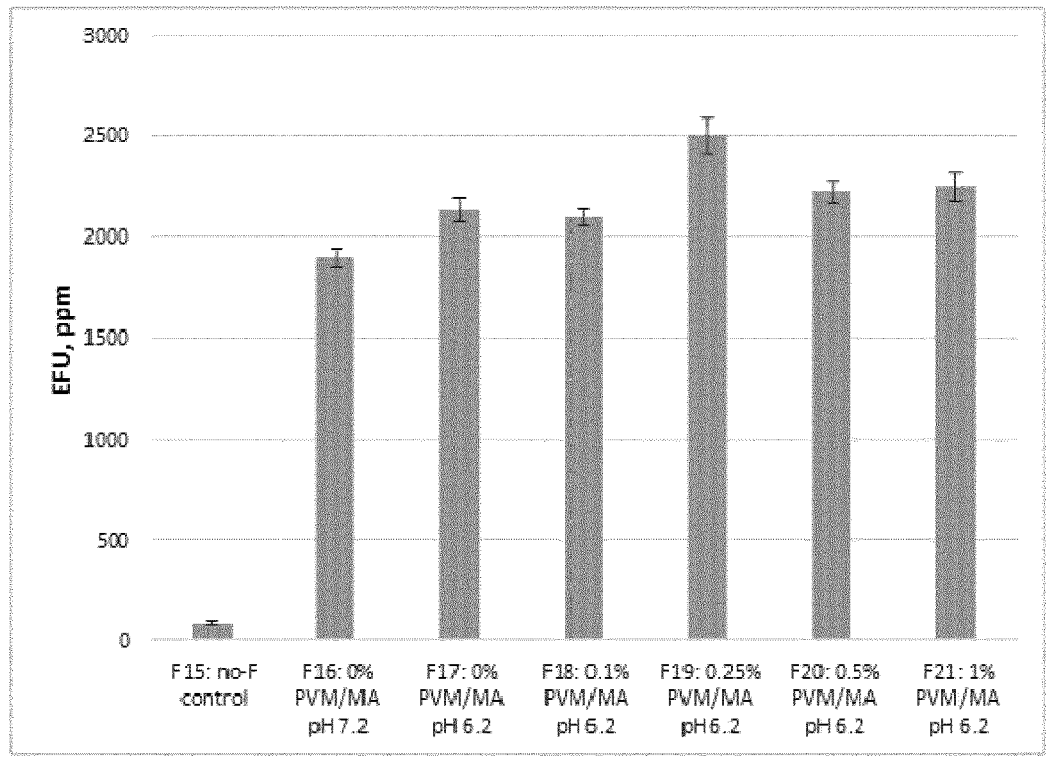
Figure 2: Effect of PVM/MA (pH 6.2) on ESR (mean, ± s.e.)
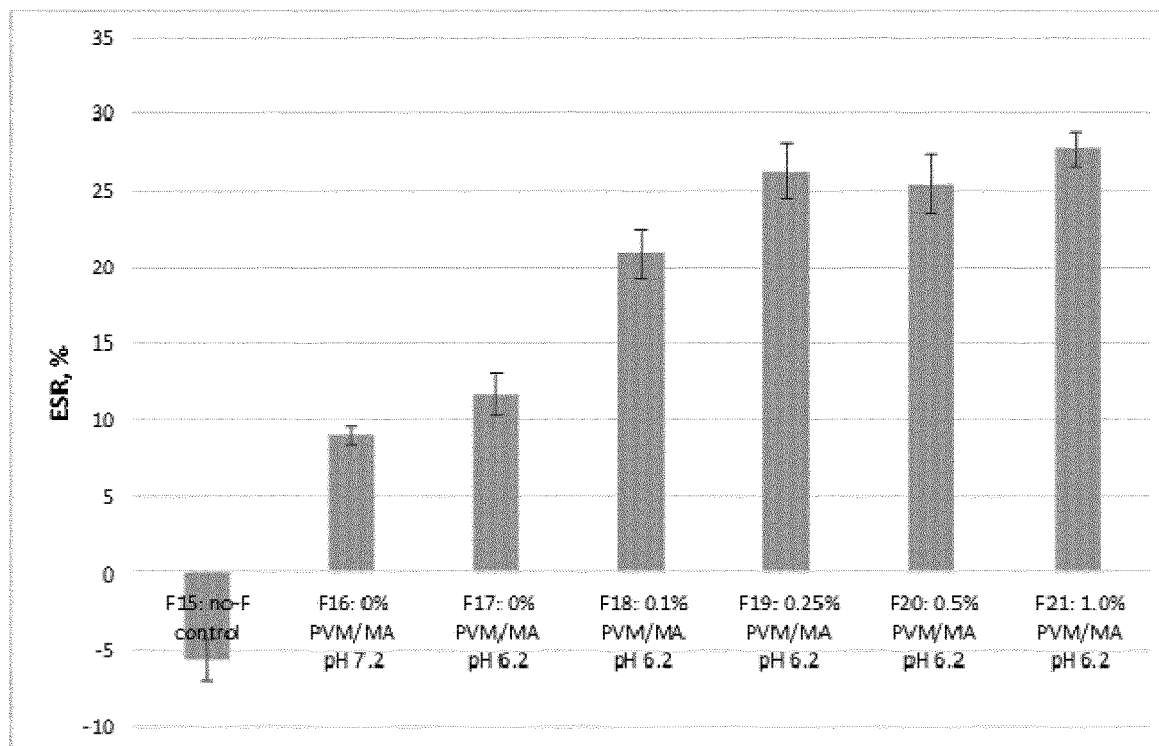

Figure 3: Results of TMR Study
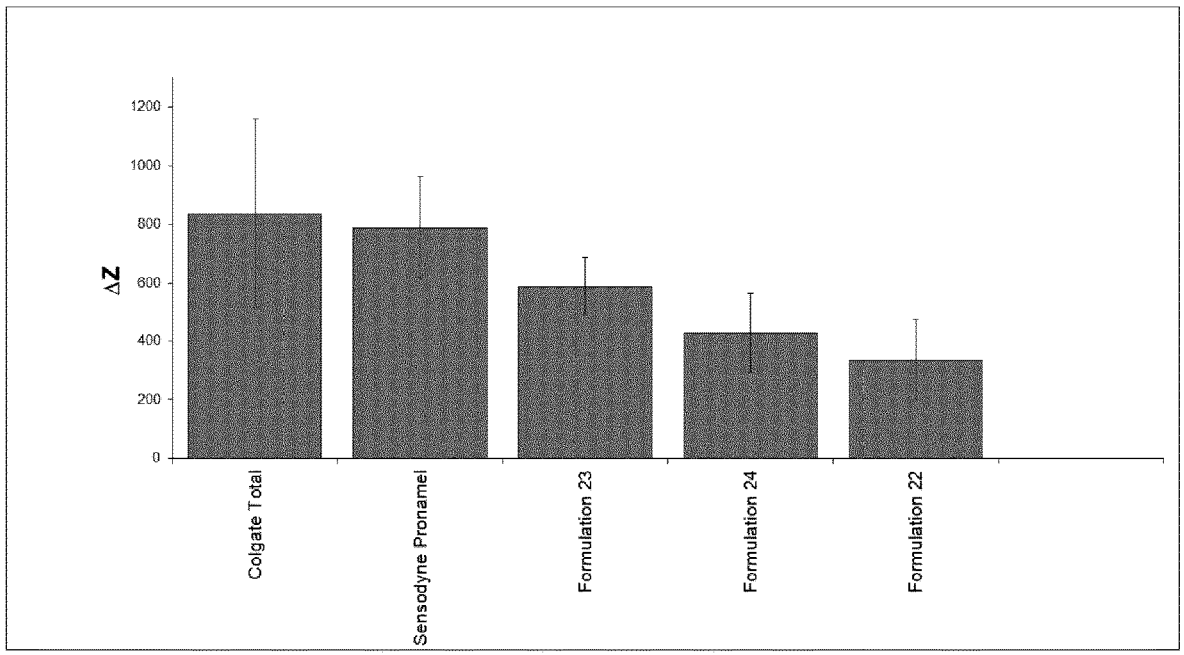
Figure 4. Tissue Loss data after treatment of Human Enamel with dentifrices followed by an erosive challenge.
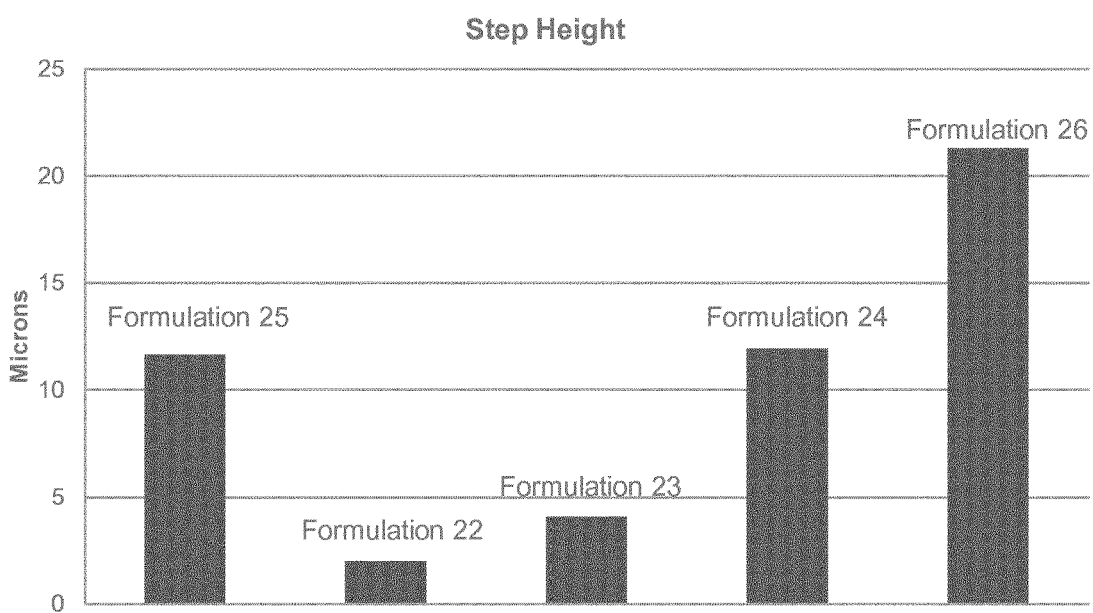

Figure 5: Enamel Surface Roughness data after treatment of Human Enamel with dentifrices followed by an erosive challenge.
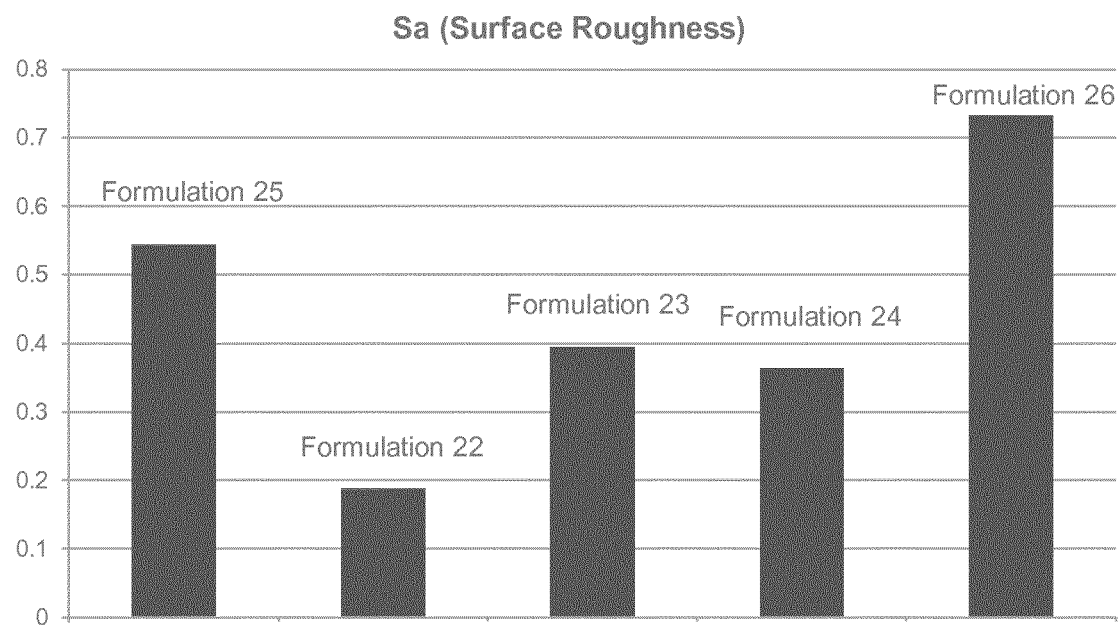

DENTIFRICE COMPRISING A PVM-MA COPOLYMER AND A SOURCE OF FREE FLUORIDE IONS

This application is a 371 of International Application No. PCT/EP2019/067790, filed 3 Jul. 2019, which claims the priority of GB Application No. GB 1811065.0, filed 5 Jul. 2018 which is incorporated herein in its entirety.

FIELD OF THE INVENTION

The present invention relates to a dentifrice composition for strengthening and protecting enamel of natural teeth, thereby providing protection against acidic challenges. A composition according to the invention comprises a source of free fluoride ions and a low amount, typically in the range from 0.1% to less than 2% by weight of the composition, for example, from 0.1% to less than 0.5% by weight, of a copolymer of methyl vinyl ether (MVE) with maleic anhydride or acid, and wherein the composition has a slurry pH from 6.0 to 7.5. The composition is free of particular carboxylic acid(s) or alkali metal salt(s) thereof. Specifically a composition according to the invention is free of a carboxylic acid or alkali metal salt thereof wherein the acid is selected from the list of malonic acid, glutaric acid, tartaric acid and lactic acid and mixtures thereof.

BACKGROUND OF THE INVENTION

Tooth mineral is composed predominantly of calcium hydroxyapatite, $Ca_{10}(PO_4)_6(OH)_2$, which may be partially substituted with anions such as carbonate or fluoride, and cations such as zinc or magnesium. Tooth mineral may also contain non-apatitic mineral phases such as octacalcium phosphate and calcium carbonate.

Tooth decay may occur as a result of dental caries, which is a multifactorial disease where bacterial acids such as lactic acid produced by metabolism of dietary sugars leads to sub-surface demineralisation that does not fully remineralise in between sugar exposures, resulting in progressive tissue loss and eventually cavity formation. The presence of a plaque biofilm is a prerequisite for dental caries, and acidogenic bacteria such as *Streptococcus mutans* may become pathogenic when levels of sugars (i.e. easily fermentable carbohydrate such as sucrose), are elevated for extended periods of time.

Even in the absence of a plaque biofilm, loss of dental hard tissues can occur as a result of acid erosion and/or physical tooth wear; these processes are believed to act synergistically. Exposure of the dental hard tissues to acid can cause demineralisation, resulting in surface softening and a decrease in mineral density. This softened mineral is vulnerable to wear from physical contact. Under normal physiological conditions, partially demineralised tissues self-repair through the remineralising effects of saliva. Saliva is supersaturated with respect to calcium and phosphate, and in healthy individuals, saliva secretion serves to wash out the acid challenge, and to raise the pH so as to alter the equilibrium in favour of mineral deposition.

Dental erosion (i.e. acid erosion or acid wear) is a surface phenomenon that involves demineralisation, and ultimately complete dissolution of the tooth surface by acids that are not of bacterial origin. Most commonly the acid will be of dietary origin, such as citric acid from fruit or carbonated drinks, phosphoric acid from cola drinks and acetic acid such as from vinaigrette. Dental erosion may also be caused by repeated contact with hydrochloric acid (HCl) produced by the stomach, which may enter the oral cavity through an involuntary response such as gastroesophageal reflux, or through an induced response as may be encountered in sufferers of bulimia.

Tooth wear (i.e. physical tooth wear) is caused by attrition and/or abrasion. Attrition occurs when tooth surfaces rub against each other, a form of two-body wear. An often-dramatic example is that observed in subjects with bruxism, a tooth-grinding habit during sleep where the applied forces are high, and is characterised by accelerated wear, particularly on the occlusal surfaces. Abrasion typically occurs as a result of three-body wear, and the most common example is that associated with brushing with a toothpaste. In the case of fully mineralised enamel, levels of wear caused by commercially available toothpastes are minimal and of little or no clinical consequence. However, if enamel has been demineralised and softened by exposure to an erosive challenge, the enamel becomes more susceptible to wear. Enamel is thinnest at its junction with the dentine, which in health is located just below the gum margin. However, gum recession (especially associated with ageing) can expose the enamel-dentine junction and wear of enamel in this region can expose dentine, leading to hypersensitivity, as described below.

Dentine is a vital tissue that in vivo is normally covered by enamel or cementum depending on the location i.e. crown versus root respectively. Dentine has a much higher organic content than enamel and its structure is characterised by the presence of fluid-filled tubules that run from the surface of the dentine-enamel or dentine-cementum junction to the pulp interface. Dentine is much softer than enamel and consequently is more susceptible to wear. Subjects with exposed dentine should avoid the use of highly abrasive toothpastes. Again, softening of dentine by an erosive challenge will increase susceptibility of the tissue to wear. It is widely accepted that the origins of dentine hypersensitivity relate to changes in fluid flow in exposed tubules, (the hydrodynamic theory), that result in stimulation of mechanoreceptors thought to be located close to the pulp interface. Not all exposed dentine is sensitive since it is generally covered with a smear layer; an occlusive mixture comprised predominantly of mineral and proteins derived from dentine itself, but also containing organic components from saliva. Over time, the lumen of the tubule may become completely occluded with mineralised tissue. The formation of reparative dentine in response to trauma or chemical irritation of the pulp is also well-documented. Nonetheless, an erosive challenge can remove the smear layer and tubule "plugs" releasing dentinal fluid flow, making the dentine much more susceptible to external stimuli such as hot, cold and pressure. As previously indicated, an erosive challenge can also make the dentine surface much more susceptible to wear. In addition, dentine hypersensitivity worsens as the diameter of the exposed tubules increases, and since the tubule diameter increases as one proceeds in the direction of the pulp interface, progressive dentine wear can result in an increase in hypersensitivity, especially in cases where dentine wear is rapid.

Erosion and/or acid-mediated tooth wear are therefore primary aetiological factors in the development of dentine hypersensitivity.

It has been claimed that an increased intake of dietary acids, and a move away from formalised meal times, has been accompanied by a rise in the incidence of dental erosion and tooth wear in the populations of developed countries. In view of this, oral care compositions which can help prevent dental erosion and tooth wear and which provide protection from dental caries would be advantageous.

Oral care compositions often contain a source of fluoride ions for promoting remineralisation of teeth and for increasing the acid resistance of dental hard tissues. To be effective the fluoride ions must be available for uptake into the dental hard tissues being treated.

The use of fluoride-containing dentifrices formulated at substantially neutral pH, have been described in the art for remineralizing and strengthening teeth. WO2006/1000071 (Glaxo Group Ltd) discloses dentifrice compositions that comprise, amongst other ingredients, a fluoride ion source, and have a pH in the range 6.5 to 7.5. Such compositions have been commercialized as SENSODYNE Pronamel toothpaste for use in protecting teeth against dietary acidic challenges.

The use of copolymers based on methyl vinyl ether and maleic acid in oral care compositions is known in the art. U.S. Pat. No. 4,485,090 discloses dentifrice compositions comprising a polymeric anionic membrane-forming material such as "Gantrez A N". According to U.S. Pat. No. 4,485,090 the material attaches itself to tooth surfaces and forms a substantially continuous barrier thereon by complexing with calcium present in the teeth. The barrier formed is described as substantially reducing elution of a previously applied therapeutic agent (e.g. dental fluoride treatment), thereby prolonging the effectiveness of such agent. According to U.S. Pat. No. 4,485,090, compositions of the invention therein need only be applied periodically (e.g. once daily) in order to achieve the desired reduction in elution and resultant control of caries and plaque.

US2004/0146466 (Baig et al) discloses methods of treating and protecting teeth against erosion by use of oral compositions comprising polymeric mineral surface active agents, metal ions such as stannous and zinc and combinations thereof. Polymeric mineral surface active agents described include synthetic anionic polymers including polyacrylates and copolymers of maleic anhydride or acid and methyl vinyl ether (e.g. Gantrez). Effective amounts of a polymeric mineral surface active agents are described as ranging from about 1% to about 35%, preferably from about 2 to about 30%, more preferably from about 5% to about 25%, and most preferably from about 6% to about 20% by weight of the total oral composition.

WO2007/069429 (Lion Corporation) discloses toothpaste compositions containing (A) from 0.3 to 1.2% by mass of at least one linear and water-soluble polyphosphate represented by the general formula $M_{n+2}P_nO_{3n+1}$ (wherein M represents Na or K; and n is an integer of 2 or 3), (B) from 0.1% to 2.0% by mass of a methyl vinyl ether/maleic anhydride copolymer, a 2.0% by mass aqueous solution of which has a viscosity of from 5 to 1000 mPa·s at 25° C. and pH 7.0, (C) from 0.6 to 2.0% by mass of a lauryl sulphate, and (D) from 0.2 to 1.0% by mass of a betaine type amphoteric surfactant, and the composition ratio by mass (C)/(D) ranging from 1 to 4. Such compositions are described as causing low irritation of the oral mucosa and as providing favourable foaming in use, as well as having an excellent effect on preventing the adhesion of stains to tooth surfaces.

WO2011/094499 (Colgate-Palmolive Company) discloses anti-erosion oral care formulations comprising a copolymer of a methyl vinyl ether and a maleic anhydride, such as Gantrez, and a metal compound or salt that becomes more soluble at acidic pH. According to WO2011/094499, a mucoadhesive polymer, such as Gantrez, may be incorporated into the orally acceptable vehicle in an amount ranging from 0.01 to 20% by weight, preferably 0.1 to 10% by weight and most preferably from 0.5 to 7% by weight of component. A "Low Polymer Formulation" and a "High Polymer Formulation" exemplified in WO2011/094499 comprises, respectively 0.5% and 2.0% by weight Gantrez.

A Technical Information Sheet, Bulletin VC-862A, published by Ashland Speciality Chemicals, reported that superior acid erosion resistance of enamel had been observed in an in vitro study, following pre-treatment of the enamel with a toothpaste containing 2% Gantrez S-97 polymer, and that the presence of the Gantrez was believed to be the primary reason for the improvement observed in reducing acid erosion.

In one aspect the present invention is based on the discovery that a low amount, in the range of 0.1% to less than 2% by weight, for example, from 0.1% to less than 0.5% by weight, of a copolymer of methyl vinyl ether with maleic anhydride or acid, can be advantageously incorporated into a dentifrice composition comprising a free source of fluoride ions. In particular, a specific low amount of the copolymer (from 0.2% to 0.3% by weight, exemplified herein by about 0.25% by weight) has been observed to provide a significant improvement in fluoride uptake (e.g. as compared to a formulation containing no copolymer) whilst at the same time providing an enamel solubility reduction similar to that achieved with compositions comprising significantly more (i.e. two or four times more) of the copolymer.

SUMMARY OF THE INVENTION

In one aspect the invention provides a dentifrice composition comprising a source of free fluoride ions; and from 0.1% to less than 2% by weight of the composition, for example, from 0.1% to less than 0.5% by weight of the composition of a copolymer of methyl vinyl ether with maleic anhydride or acid; and wherein the composition has a slurry pH from 6.0 to 7.5, and wherein the composition is free of a carboxylic acid or alkali metal salt thereof wherein the acid is selected from the group consisting of malonic acid, glutaric acid, tartaric acid, lactic acid and mixtures thereof.

Such compositions are of use in protecting teeth against dental erosion. Such compositions are also of use in protecting teeth against dental caries.

BRIEF DESCRIPTION OF THE DRAWINGS

FIG. 1: Effect of PVM/MA (pH 6.2) on EFU
FIG. 2: Effect of PVM/MA (pH 6.2) on ESR
FIG. 3: Results of TMR Study
FIG. 4. Tissue Loss data after treatment of Human Enamel with dentifrices followed by an erosive challenge
FIG. 5. Enamel Surface Roughness data after treatment of Human Enamel with dentifrices followed by an erosive challenge.

DETAILED DESCRIPTION OF THE INVENTION

A composition according to the invention comprises a source of free fluoride ions. By the term, "a source of free fluoride ions", is meant a compound which contains fluoride ions. A source of free fluoride ions is not an alkali metal monofluorophosphate such as sodium monofluorophosphate. Suitable examples of a source of free fluoride ions include an alkali metal fluoride such as sodium or potassium fluoride, polyvalent metal ion fluoride salts such as stannous fluoride, or salts of fluoride with cationic organic ions such as ammonium fluoride or bis-(hydroxyethyl) amino-propyl-N-hydroxyethyloctadecylamine-dihydrofluoride, (amine fluoride) or a mixture thereof. Suitably the source of free fluoride ions is used in an amount to provide from 25 to 5000 ppm of fluoride ions, preferably from 100 to 1500 ppm. In one embodiment the source of free fluoride ions is stannous fluoride. In one embodiment the source of free fluoride ions is an alkali metal fluoride such as sodium fluoride. Suitably the composition contains from 0.05% to 0.5% by weight of sodium fluoride, e.g. 0.1% by weight (equating to 450 ppm of fluoride ions), 0.205% by weight (equating to 927 ppm of fluoride ions), 0.2542% by weight (equating to 1150 ppm of fluoride ions) or 0.3152% by weight (equating to 1426 ppm of fluoride ions).

A composition according to the invention is mildly acidic, neutral or mildly alkaline i.e. has a slurry pH in the range from 6.0 to 7.5, for example from pH 6.1 to 7.4, 6.2 to 7.3, or 6.2 to 7.2. In one embodiment the composition has a pH of about 6.2. In a further embodiment the composition has a pH of about 7.0. The pH referred to is that measured when the dentifrice composition is slurried with water in a 1:3 weight ratio of the composition to water. Suitably the slurry is prepared by slurring the dentifrice composition with water in a weight ratio of one part dentifrice composition and three parts distilled water. The pH is determined using a standard pH meter.

Suitably a dentifrice composition of the invention comprises a pH modifying agent to adjust the pH of the composition to the desired pH. Suitable pH modifying agents include alkali metal hydroxides such as sodium hydroxide and potassium hydroxide, or inorganic acids such as hydrochloric acid or sulphuric acid. In one embodiment the pH modifying agent is sodium hydroxide, such as a 10.2% sodium hydroxide solution. A pH modifying agent may be used in an amount from 0.005% to 5% by weight of the composition, such as from 0.01% to 2% or 0.02% to 1% by weight of the composition.

A composition according to the invention comprises a surface protection agent which is a copolymer of methyl vinyl ether (MVE) with maleic anhydride or acid. In one embodiment the surface protection agent is a copolymer of MVE with maleic acid. In general the copolymer is a linear copolymer comprising alternating units of MVE and maleic anhydride or acid. In one embodiment the copolymer comprises a 1:4 to 4:1 ratio of MVE:maleic anhydride or acid, such as a 1:1 ratio of MVE:maleic anhydride or acid i.e. the MVE content is about 50 mole % and the maleic anhydride or acid content is about 50 mole %. In one embodiment the copolymer is the acid form of a copolymer of MVE with maleic anhydride wherein the anhydride is fully or partially hydrolysed, e.g. following co-polymerization to provide the corresponding acid. In one embodiment the copolymer has a molecular weight in the range 100,000 to 2,000,000 e.g. from 500,000 to 1,900,000 or from 1,000,000 to 1,800,000. Suitably a copolymer for use in the invention is available commercially under the trade name GANTREZ® such as GANTREZ® S-97 HSU solution (Mw 1,500,000), GANTREZ® S-97 BF (Mw 1,200,000), GANTREZ® S-96 (Mw 700,000) and GANTREZ® S-95 (Mw 150,000), all of which are copolymers of MVE with maleic acid. In one embodiment the copolymer is GANTREZ® S-97 which is a copolymer of MVE with maleic acid having an approximate molecular weight of 1,200,000 or 1,500,000.

GANTREZ® S-97 may be provided in the form of a solid (powder) or as a liquid such as an aqueous solution e.g. GANTREZ ° S-97 HSU solution. In one embodiment the copolymer comprises a GANTREZ® polymer with the following structure and below indicated properties:

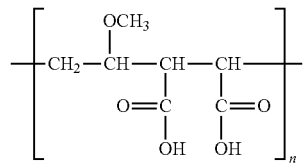

Di-basic acid with $pKa_1=3.5$, $pK\ a_2=6.5$

| Property | Gantrez S-97 BF | Gantrez S-97 HSU Solution |
|---|---|---|
| Appearance @ 25° C. | White to off-white, free flowing powder | Slightly hazy viscous solution |
| % Solids (Active) | 94 | 15-17 |
| % Moisture | ≤6 | 85-83 |
| Approx. Molecular Weight | 1,200,000 | 1,500,000 |

Suitably the rheological properties of the copolymer can be modified by the addition of salts and bases. GANTREZ® copolymers are available commercially from various sources including Ashland Speciality Chemicals, Bound Brook, N.J. 08805, USA and International Specialty Products, Wayne, NJ, USA.

It is a challenge to provide a dentifrice composition that delivers an enhanced fluoridation benefit when the composition comprises a surface protection agent (i.e. a copolymer of use in the invention as hereinabove defined), intended to provide a shield or barrier over the surface of tooth enamel to protect enamel from acid attack. This is because of surface coverage of sites on the tooth surface by the agent where fluoridation typically takes place. Advantageously in the present invention, the copolymer is combined with a source of fluoride ions without adversely impacting upon the delivery of fluoride to the dental enamel. In one embodiment, fluoride uptake is significantly enhanced in the presence of the copolymer. Whilst not being bound by theory, the polymer may serve to facilitate fluoride uptake by the enamel and/or may serve to prolong fluoride contact at the tooth surface, allowing for formation of fluoroapatite and facilitating remineralization. Advantageously a composition according to the present invention seeks to provide not only an effective physical barrier that protects enamel surface from acid attack and consequently inhibits demineralization of the tooth surface, but that also provides, through the action of fluoride, effective remineralization of acid-damaged enamel surfaces.

The copolymer is used in an amount from 0.1% to less than 2% by weight of the composition such as from 0.1% to less than 1.5% by weight of the composition or from 0.1% to 1% by weight of the composition or from 0.1% to less than 1% by weight of the composition. In one embodiment the copolymer is used in an amount from 0.1% to 0.5% by weight of the composition or from 0.1% to less than 0.5% by weight of the composition, such as from 0.15% to 0.4% or from 0.2% to 0.3% by weight of the composition. In one embodiment the copolymer is used in an amount of about 0.25% by weight of the composition. It has been surprisingly found in in vitro testing, reported herein, that when such a particular low amount of copolymer is used, a significant improvement may be observed with respect to inhibition of demineralization and uptake of fluoride. In one embodiment the copolymer is used in amount of about 0.25% by weight of the composition and the composition has a slurry pH of 6.0 to 7.5 such as about 6.2. In one embodiment the copolymer is used in amount of about 0.25% by weight of the composition and the composition has a slurry pH of about 7.0.

In one embodiment a composition of the invention does not comprise stannous ions and/or zinc ions. For example in one embodiment a composition of the invention does not comprise from about 0.001% to about 5% of metal ions wherein the metal ions comprise at least 0.001% of stannous ions and optionally from about 0.001% to about 4% of zinc ions. In one embodiment a composition according to the invention does not comprise a salt or compound of calcium and zinc that becomes more soluble at acidic pH, as disclosed in WO 2011/094499. In one embodiment the composition does not comprise a calcium or zinc compound or salt thereof.

Compositions of the present invention may contain appropriate formulating agents such as dental abrasives, surfactants, thickening agents, humectants, flavouring agents, sweetening agents, opacifying or colouring agents, preservatives and water, selected from those conventionally used in the oral care composition art for such purposes.

Examples of suitable dental abrasives include silica abrasives such as those marketed under the following trade names Zeodent, Sident, Sorbosil or Tixosil by Huber, Degussa, Ineos and Rhodia respectively. The silica abrasive should be present in an amount sufficient to ensure adequate cleaning of teeth by the dentifrice whilst not promoting abrasion of teeth.

The silica abrasive is generally present in an amount up to 15% by weight of the total composition, for example from 2% to 10% by weight, and preferably at least 5% for example from 5% to 7% by weight, especially 6% by weight of the total composition. Reducing the level of silica abrasive has the advantage of not only lowering the abrasivity of the dentifrice but also minimising any interaction of the abrasive with fluoride ions thereby increasing the availability of free fluoride ions.

Suitable surfactants for use in the present invention include amphoteric surfactants for example, long chain alkyl betaines, such as the product marketed under the tradename 'Empigen BB' by Albright & Wilson, and preferably long chain alkyl amidoalkyl betaines, such as cocamidopropylbetaine, or low ionic surfactants such as sodium methyl cocoyl taurate, which is marketed under the trade name Adinol CT by Croda, or mixtures thereof. An amphoteric surfactant can be used alone as sole surfactant or can be combined with a low ionic surfactant. Suitably the surfactant is not a $C_{10-18}$ alkyl sulphate surfactant, such as sodium lauryl sulphate, commonly used in oral compositions.

Suitably, the surfactant is present in the range 0.1% to 10%, preferably 0.1% to 5% and more preferably 0.5% to 1.5% by weight of the total composition.

Suitable thickening agents include, for instance, nonionic thickening agents such as, for example, (C1-6)alkylcellulose ethers, for instance methylcellulose; hydroxy(C1-6)alkylcellulose ethers, for instance hydroxyethylcellulose and hydroxypropylcellulose; (C2-6)alkylene oxide modified (C1-6)alkylcellulose ethers, for instance hydroxypropyl methylcellulose; and mixtures thereof. Other thickening agents such as natural and synthetic gums or gum like material such as Irish Moss, xanthan gum, gum tragacanth, sodium carboxymethylcellulose, polyvinyl pyrrolidone, starch and thickening silicas may also be used. Preferably the thickening agent is mixture of a thickening silica and xanthan gum.

Advantageously the thickening agent is present in the range 0.1% to 30%, preferably 1% to 20%, more preferably 5% to 15% by weight of the total composition.

Suitable humectants for use in compositions of the invention include for instance, glycerin, xylitol, sorbitol, propylene glycol or polyethylene glycol, or mixtures thereof; which humectant may be present in the range from 10% to 80%, preferably 20% to 60%, more preferably 25% to 50% by weight of the total composition.

A preferred opacifying agent is titanium dioxide which may be present in the range 0.05% to 2%, preferably 0.075% to 0.2%, for example 0.1% by weight of the total composition. This amount enhances the visual appearance of the composition.

Flavouring agents that may be used in a composition of the invention include various flavouring aldehydes, esters, alcohols, and similar materials, as well as menthol, carvone and aethole as well as mixtures thereof. Examples of essential oils include spearmint, peppermint, wintergreen, sassafras, clove, sage, eucalyptus, marjoram, cinnamon, lemon, lime, grapefruit and orange. Suitably the flavouring agent may be used in an amount ranging from 0.01% to 4% such as 0.1% to 3% or 0.5% to 2% by weight of the composition.

Sweetening agents that may be used in a composition of the invention include, for example, sucrose, glucose, saccharin, sucralose, dextrose, levulose, lactose, mannitol, sorbitol, fructose, maltose, xylitol, saccharin salts (e.g. sodium saccharin) acesulfame and mixtures thereof. In one embodiment sodium saccharin is used as the sweetening agent. Suitably the sweetening agent may be used in an amount ranging from 0.005% to 10% such as 0.01% to 3% or 0.1% to 1% by weight of the composition.

Dentifrice compositions of the present invention are aqueous compositions. Water may make up the balance of the dentifrice composition. In one embodiment, the composition comprises 5% to 80% such as 10% to 60%, 15% to 40% or 20% to 35% by weight water. This amount of water includes the free water which is added plus that amount which is introduced with other components of the dentifrice composition, such as with sorbitol. Dentifrice compositions of the present invention are typically formulated in the form of toothpastes or gels.

Additional oral care actives may be included in the compositions of the present invention.

Compositions of the present invention may further comprise a desensitising agent for combating dentine hypersensitivity. Examples of desensitising agents include a tubule blocking agent or a nerve desensitising agent and mixtures thereof, for example as described in WO 02/15809.

Suitable tubule blocking agents include strontium salts such as strontium chloride, strontium acetate or strontium nitrate. Suitably the strontium salt is used in an amount generally from 5% to 15% by weight of the composition.

In one embodiment the tubule blocking agent is a bioactive glass. Suitably the bioactive glass consists of 45% by weight silicon dioxide, 24.5% by weight sodium oxide, 6% by weight phosphorus oxide, and 24.5% by weight calcium oxide. One such bioactive glass is available commercially under the trade name, NOVAMIN, also known as 45S5 BIOGLASS. Suitably the bioactive glass is used in an amount generally from 1% to 10% by weight of the composition.

In one embodiment the tubule blocking agent is stannous fluoride. Stannous fluoride, through hydrolysis and oxidation reactions, forms insoluble metal salts that precipitate in dentinal tubules and on the dentine surface to provide effective relief from dentine hypersensitivity. Stannous fluoride may also be used to provide a source of fluoride capable of delivering protection from caries and plaque/gingivitis.

Suitable nerve desensitizing agents include potassium salts such as potassium citrate, potassium chloride, potassium bicarbonate, potassium gluconate and especially potassium nitrate. A desensitising amount of a potassium salt is generally between 2 to 8% by weight of the total composition, for example 5% by weight of potassium nitrate can be used.

Compositions of the present invention may comprise a whitening agent, for example selected from a polyphosphate, e.g. sodium tripolyphosphate (STP) and/or any additional silica abrasive present may have high cleaning properties. STP may be present in an amount from 2% to 15%, for example from 5% to 10% by weight of the total composition.

The composition of the present invention is suitable for containing in and dispensing from an aluminium-plastic laminate tube or a plastic pump as conventionally used in the art.

Compositions of the present invention may be prepared by admixing the ingredients in the appropriate relative amounts in any order that is convenient and adjusting the pH to give a desired value.

An exemplary dentifrice composition according to the invention comprises:

a source of free fluoride ions such as sodium fluoride in an amount from 0.05% to 0.5%;

a copolymer of MVE with maleic anhydride or acid such as GANTREZ® S-97 in an amount from 0.1% to less than 0.5%; and wherein the composition has a slurry pH from 6.0 to 7.5.

The present invention provides a composition as hereinbefore defined for use in protecting teeth against dental erosion. The present invention further provides a composition as hereinbefore defined for use in protecting teeth against dental caries.

The present invention provides a composition as hereinbefore defined for use in the treatment and/or inhibition of dental erosion on a dental surface. The present invention provides a composition as hereinbefore defined for use in the treatment and/or inhibition of caries on a dental surface.

The present invention also provides a method for protecting teeth against dental erosion which comprises applying an effective amount of a composition as hereinbefore defined to an individual in need thereof. The present invention also provides a method for protecting teeth against dental caries which comprises applying an effective amount of a composition as hereinbefore defined to an individual in need thereof.

The present invention provides a method for the treatment and/or inhibition of dental erosion on a dental surface, comprising contacting the dental surface with a composition as hereinbefore defined.

The present invention provides a method for the treatment and/or inhibition of dental caries on a dental surface, comprising contacting the dental surface with a composition as hereinbefore defined. The invention is further illustrated by the following Examples.

Example 1

Dentifrice compositions Formulations F15-F21 described below (see Table 1) were prepared.

TABLE 1

Formulations

| Ingredients | F15 (Control) % w/w | F16 (Control) % w/w | F17 (Control) % w/w | F18 % w/w | F19 % w/w | F20 % w/w | F21 % w/w |
|---|---|---|---|---|---|---|---|
| Water | 31.5971 | 31.4458 | 31.2522 | 31.29 | 30.03 | 27.92 | 23.69 |
| Sorbitol (70% w/w) | 30.0000 | 30.0000 | 30.0000 | 30.00 | 30.00 | 30.00 | 30.00 |
| Dental Silica | 18.0000 | 18.0000 | 18.0000 | 18.00 | 18.00 | 18.00 | 18.00 |
| Glycerin | 8.0000 | 8.0000 | 8.0000 | 8.00 | 8.00 | 8.00 | 8.00 |
| Potassium Nitrate | 5.0000 | 5.0000 | 5.0000 | 5.00 | 5.00 | 5.00 | 5.00 |
| PEG 400 (PEG-8) | 3.0000 | 3.0000 | 3.0000 | 3.00 | 3.00 | 3.00 | 3.00 |
| Cocamidopropyl Betaine | 1.2000 | 1.2000 | 1.2000 | 1.20 | 1.20 | 1.20 | 1.20 |
| Flavour | 1.2000 | 1.1000 | 1.2000 | 1.20 | 1.20 | 1.20 | 1.20 |
| Xanthan gum | 0.8000 | 0.8000 | 0.8000 | 0.80 | 0.80 | 0.80 | 0.80 |
| Saccharin, sodium | 0.3000 | 0.3000 | 0.3000 | 0.30 | 0.30 | 0.30 | 0.30 |
| Sodium fluoride | — | 0.2542 | 0.2542 | 0.25 | 0.25 | 0.25 | 0.25 |
| Titanium Dioxide | 0.1000 | 0.1000 | 0.1000 | 0.10 | 0.10 | 0.10 | 0.10 |
| PVM/MA* Copolymer 16.5% solution (Actual amount) | — | — | — | 0.61 (0.1) | 1.52 (0.25) | 3.03 (0.5) | 6.06 (1.1) |
| 10.2% NaOH solution | 0.8039 | 0.8000 | — | 0.25 | 0.60 | 1.20 | 2.40 |
| Total | 100.0000 | 100.0000 | 100.0000 | 100.00 | 100.00 | 100.00 | 100.00 |

*PVM/MA = polyvinyl methyl ether/maleic acid

Example 2

Enamel Fluoride Uptake (EFU)

This example describes an enamel fluoride uptake study carried out on dentifrice compositions (F15-F21) described in Table 1.

Method

The EFU test procedure was based on Procedure 40 described in the United States Food and Drug Administration (FDA) testing procedures. In the present case, the incipient lesion was formed using 0.1M lactic acid pH 5.0 containing 0.2% w/v polyacrylic acid (Carbopol 907) that was 50% saturated with hydroxyapatite.

Sound, upper, central, bovine incisors were cleaned of all adhering soft tissue. A core of enamel 3 mm in diameter was prepared from each tooth using a hollow-core diamond drill bit under running water. Specimens were embedded in the end of a plexiglass rod using methyl methacrylate, and polished with 600 grit wet/dry paper and then with microfine Gamma Alumina. Twelve specimens per group were used in the study.

Each enamel specimen was etched by immersion into 0.5 ml of 1M perchloric acid ($HClO_4$) solution for 15 seconds with continuous agitation.

The fluoride content of this solution was determined by using a fluoride electrode to determine the background fluoride content of the enamel specimens.

The specimens were once again ground and polished as described above. An incipient lesion was formed in each enamel specimen by immersion into a 0.1M lactic acid/0.2% Carbopol 907 solution for 24 hours at 37° C. These specimens were rinsed with water and stored in a humid environment until used.

The specimens were immersed into 25 ml of their assigned 1 part dentifrice and 3 parts (w/) distilled water slurry supernatant with constant stirring (350 rpm) for 30 minutes. Following treatment, the specimens were rinsed with water. One layer of enamel was removed from each specimen by etching as above. The etch solution was analyzed for fluoride (ion-specific electrode) and calcium. The pre-treatment fluoride (indigenous) level of each specimen was then subtracted from the post-treatment value to determine the change in enamel fluoride due to the test treatment.

Statistical Analyses

Statistical analyses of the individual means were performed with a one-way analysis of variance model. Significance of differences was analyzed by the Student Newman-Keuls test.

Results

The results are shown in Table 2, and FIG. 1.

TABLE 2

EFU values of dentifrice compositions comprising PVM/MA Copolymer

| Formulation | EFU | s.e. |
| --- | --- | --- |
| Formulation 15 | 86 | 7 |
| Formulation 16 (pH 7.2) | 1896 | 50 |
| Formulation 17 (adjusted to pH 6.2) | 2136 | 62 |
| Formulation 18 (adjusted to pH 6.2) | 2096 | 45 |
| Formulation 19 (adjusted to pH 6.2) | 2498 | 87 |
| Formulation 20 (adjusted to pH 6.2) | 2219 | 55 |
| Formulation 21 (adjusted to pH 6.2) | 2249 | 73 |

At 5% significance level, all fluoride-containing formulations were statistically significantly greater than the fluoride-free placebo. The formulation containing 0.25% PVM/MA copolymer (Formulation 19) was statistically significantly superior to all other formulations tested. There were no significant differences between the other formulations.

Conclusion

All fluoride-containing formulations were superior to the fluoride-free placebo. There was evidence to suggest that use of 0.25% polymer was surprisingly favourable to EFU.

Example 3—Enamel Solubility Reduction Study

Dentifrice compositions Formulations 15-21 described above in Table 1 were prepared and ESR determined as described below. The results are shown in Table 3, and FIG. 2.

Tooth Preparation

Three sound human molars were placed in wax so that only the enamel surfaces were exposed, then cleaned and polished. Twelve sets of three teeth each were prepared for the study.

Lactate Buffer Preparation

A 0.1 M lactic acid solution buffered to pH 4.5 was prepared.

Deprotection

Teeth surfaces were etched in 0.1 M lactate buffer solution for two one-hour periods at room temperature, then rinsed well with water.

Pre-Treatment Etch

The test was performed using preheated (37° C.) tooth sets and lactate buffer in an incubator. The acid-pre-treated teeth sets were mounted on the ends of acrylic rods with molten wax. A small hole was drilled in each container lid to accommodate the plastic rod to which the tooth sets were mounted. A 40 ml portion of 0.1 M lactic acid buffer was placed in each container. The rod of the first tooth set will be pushed through the hole in the lid, placed in the first container and adjusted so that all enamel surfaces were immersed into the lactic acid solution. After 15 minutes of stirred exposure to the buffered lactate solution, the tooth sets were removed from the container and rinsed in water. The lactate buffer solutions were retained and analysed for phosphorus. The tooth sets were then placed back in the 37° C. water bath in preparation for the treatment step.

Treatment

All tooth sets were treated at the same time (one for each product). A 30 ml portion of preheated dentifrice slurry was added to each container, then the teeth were immersed in the dentifrice slurry and stirred for 5 minutes. The other tooth sets were treated in the same manner with the other dentifrice slurries. At the end of treatment, the tooth sets were removed and rinsed well with water.

Post-Treatment

A second lactic acid exposure was performed by the same method as the pre-treatment etch on the dentifrice-treated samples and the treatment solutions analysed for phosphorus. The pre- and post-treatment solutions were analyzed for phosphorus using a Klett-Summerson Photoelectric Colorimeter.

The tooth sets were the etched again and the procedure repeated additional times so that each tooth set was treated with each dentifrice. The treatments were allocated in a Latin Square design to ensure treatment sequences varied.

Calculation of E.S.R.

The percent of enamel solubility reduction was calculated as the difference between the amount of phosphorus in the pre- and post-acidic solutions, divided by the amount of phosphorus in the pre-solution, multiplied by 100.

Results

TABLE 3

Results of ESR Study

| # | Sample ID | ESR | s.e. |
|---|---|---|---|
| 1 | Formulation 15 | −5.68 | 1.41 |
| 2 | Formulation 16 | 8.94 | 0.53 |
| 3 | Formulation 17 (adjusted to pH 6.2) | 11.67 | 1.37 |
| 4 | Formulation 18 (adjusted to pH 6.2). | 20.86 | 1.59 |
| 5 | Formulation 19 (adjusted to pH 6.2) | 26.23 | 1.77 |
| 6 | Formulation 20 (adjusted to pH 6.2) | 25.43 | 1.86 |
| 7 | Formulation 21 (adjusted to pH 6.2) | 27.68 | 1.15 |

All fluoride-containing dentifrices gave ESR values statistically superior to the fluoride-free placebo. A clear dose-response to PVM/MA copolymer content was observed between 0% and 0.25%. An approximately 15% increase in ESR was observed due to the presence of 0.25% PVM/MA copolymer. Above 0.25%, no further increase in ESR was observed up to at least 1% PVM/MA copolymer.

Conclusion

Addition of PVM/MA copolymer up to 0.25% caused a significant increase in enamel solubility reduction. No further increase was noted on adding higher levels of the copolymer.

Example 4—a Transverse Microradiography (TMR) Study to Quantify Mineral Loss in Incipient Lesions Following Dentifrice Treatment Dentifrice compositions according to the invention, Formulations 22-24 described below in Table 4, were prepared for use in this study. In addition, two marketed control formulations, Sensodyne Pronamel and Colgate Total were included. The TMR study detailed below was performed and the results shown in FIG. 3 and Table 5. The present model is a modification of the pH cycling model described by Featherstone et al. [1986].

Featherstone J O B, O'Reilly M M, Shariati M, Brugler S. Enhancement of remineralization in vitro and in vivo. In: Leach S A, ed. Factors Relating to Demineralisation and Remineralisation of the Teeth, pp. 23 34 (IRL Press Ltd, Oxford, 1986

TABLE 4

Formulations

| Ingredient name | F22 % w/w | F23 % w/w | F24 % w/w |
|---|---|---|---|
| Purified water | 31.66138 | 31.32615 | 30.6557 |
| Sorbitol, Liquid (Non-crystallizing) | 30 | 30 | 30 |
| Silica, Dental Type (Zeodent 153) | 12 | 12 | 12 |
| Silica, Dental Type (Zeodent 116) | 6 | 6 | 6 |
| Glycerol | 8 | 8 | 8 |
| Potassium nitrate | 5 | 5 | 5 |
| Polyethylene glycol 300 (PEG-6) | 3 | 3 | 3 |
| Cocamidopropyl betaine | 1.2 | 1.2 | 1.2 |
| Flavour | 1.2 | 1.2 | 1.2 |
| Xanthan gum | 0.8 | 0.8 | 0.8 |
| Sodium fluoride | 0.315 | 0.315 | 0.315 |
| Saccharin sodium | 0.35 | 0.35 | 0.35 |
| Titanium dioxide | 0.1 | 0.1 | 0.1 |
| Sodium hydroxide | 0.123625 | 0.20885 | 0.3793 |
| Gantrez | 0.25 | 0.5 | 1 |
| Total | 100 | 100 | 1000 | pH of formulations F22, F23 and F24 (1:3 slurry in water) = 7

Methodology

Specimen Preparation

Enamel specimens were obtained from human permanent teeth. Tooth crowns were cut into 4×4 mm specimens using a Buehler Isomet low-speed saw. The teeth were stored in thymol during the sample preparation process. Specimens were ground and polished to create flat, planar parallel dentin and enamel surfaces using a Struers Rotopol 31/Rotoforce 4 polishing unit (Struers Inc., Cleveland, Pa., USA). The dentin side of the specimens was ground flat to a uniform thickness with 500-grit silicon carbide grinding paper. The enamel side of the specimen was serially ground using 1,200, 2,400 and 4,000 grit paper. The specimens were then be polished using a 1 μm diamond polishing suspension on a polishing cloth until the enamel surface had a minimum of a 2×4 mm highly polished facet across the specimen. Resulting specimens had a thickness range of 1.7-2.2 mm. The specimens were assessed under the Nikon SMZ 1500 stereomicroscope at 20× magnifications for cracks, hypomineralized (white spots) areas or other flaws in the enamel surface that would exclude them from use in the study. An experimental window, measuring approximately 1.7×4 mm, was created on the specimens using acid-resistant, colored nail varnish (Sally Hansen Advanced Hard As Nails Nail Polish, USA), leaving sound enamel (reference) areas on either side. Prepared specimens were stored at 100% relative humidity at 4° C. until use. A total of 135 specimens were required for this study.

Microradiography

After completion of the pH cycling study, sections, approximately 100 μm in thickness, were cut from one side of the specimens and across the lesion window and sound enamel (reference) areas after lesion creation (lesion baseline) using a Silverstone-Taylor Hard Tissue Microtome (Scientific Fabrications Laboratories, USA). The sections were mounted, with an aluminum step wedge, on high resolution glass plate Type I A (Microchrome Technology Inc., San Jose, CA) and X-rayed at 20 kV and 30 mA at a distance of 42 cm for 65 min. The film was developed in Kodak d-19 developer for 3 min, placed in a stop bath (Kodak 146-4247) for 45 s, and then fixed (Kodak 146-4106) for 3 min. All plates were then rinsed in deionized water for 15 min and air-dried. Microradiographs were examined with a Zeiss EOM microscope in conjunction with the TMR software v.3.0.0.11. Sound enamel was assumed to be 87% v/v mineral.

Study Variables

All reported variables are summarized below:
 ΔZ—lesion volume (product of lesion depth and the mineral loss over that depth)
 L—lesion depth (83% mineral; i.e. 95% of the mineral content of sound enamel)

SZmax—maximum mineral density at the lesion surface zone

Specimen Randomization

Specimens were randomized into 5 treatment groups with n=24 (n=18 for Internal Control).

Specimens were assigned to 4 (3 for the internal control) stoppers with 6 specimens per stopper per treatment group.

pH Cycling Phase (15 Treatment Days)

Toothpaste slurries were prepared by mixing 1 part by weight of dentifrice with 3 parts by weight of deionized water in a beaker with a magnetic stirrer (e.g. 8 g toothpaste+24 g deionized water). A fresh slurry for each subgroup was prepared just prior to each treatment. All treatments were stirred at 350 rpm.

A demineralisation solution with the following composition was used in all treatment regimes (refreshed with every cycle):

Compound mM
- Acetic acid 75
- $CaCl_2 \times 2H_2O$ 2.0
- $KH_2PO_4$ 2.0
- (pH adjusted to 4.4 with KOH)

A pH 7 remineralization solution with the following composition was used in all treatment regimes:

Compound mM
- $CaCl_2 \times 2H_2O$ 1.5
- $KH_2PO_4$ 0.9
- KCl 130
- HEPES 20

The cyclic treatment regimen consisted of the following pH cycling regime which was repeated daily for 15 treatment days:

pH Cycling Regime:
- 1 min Treatment
- 6 h Demineralisation solution (37° C.)
- 1 min Treatment
- 16 h Remineralisation solution (37° C.)

Specimens remained in remineralization solution overnight. Specimens were not pH cycled during weekends and public holidays. The day prior to the break, specimens were exposed to the remineralization solution for 1 h after the second treatment. Then, specimens were rinsed under running deionized water and stored at approx. 4° C. and 100% relative humidity until the next pH cycling day; pH cycling then commenced as outlined above.

After each treatment with the study products or after exposure to the demineralizing solution, specimens were rinsed with running deionized water. All specimens were then placed back into the remineralisation solution.

Data Management and Statistical Analysis

The study variables $\Delta Z$, L and SZmax were calculated for each specimen. The study variables were analysed using an analysis of variance with test product as a factor. The primary endpoint is $\Delta Z$. All statistical tests were 2-sided with a nominal level of significance of $\alpha$=0.05.

Results and Conclusion

The data shown in FIG. 3 and Table 5 show that the value of AZ is lower for formulation 22, containing 0.25% Gantrez. This value of AZ is statistically lower than that of the two marketed control toothpastes and directionally lower than either of the formulations containing a higher percentage of gantrez. This lower value of $\Delta Z$ represents a shallower lesion of higher mineral content at the end of the experiment, indicating greater enamel protection by formulation 22 against the acidic challenge carried out during the experiment.

TABLE 5

Results of TMR Study

| Formulation | $\Delta Z$ |
|---|---|
| Colgate Total | 837 ± 173 |
| Sensodyne Pronamel | 789 ± 99 |
| Formulation 23 | 588 ± 136 |
| Formulation 24 | 428 ± 137 |
| Formulation 22 | 336 ± 74 |

Example 5—White Light Interferometry Analysis (Enamel Protection)

The aim of this study was to monitor and quantify the effect, in vitro, of treating human enamel with dentifrice formulations on subsequent erosion by a dietary acid. The technique of White Light Interferometry can provide rapid visualisation of surface topography. Determination of roughness parameters can be carried out in non-contact mode, and height resolution on the nanometer scale is obtainable.

Methodology

Twenty five Human Enamel specimens were polished flat and a region of their surface taped off using acid resistant tape. The specimens were then divided into five treatment groups (n=5 for each group) and immersed into one of the following dentifrice slurries (1:3 wt % in deionised water) with manual brushing for 2 minutes: Formulation 22, Formulation 23, Formulation 24, Formulation 25 or Formulation 26. Formulations 22-24 were as described in Table 4 above, and Formulations 25 and 26 are detailed in Table 5 below. Samples were then washing for 1 minute with deionised water. After dentifrice treatment, specimens were suspended in 1% citric acid, pH 3.8 for 5 minutes, without agitation. Specimens were washed with deionised water and air dried then analysed using white light interferometry.

The surface topography of the specimens was investigated using an ADE PhaseShift MicroXAM White Light Interferometer. Data was acquired from multiple areas (of size 687 µm×511 µm and 215 µm×160 µm) for each specimen. After removal of the tape mask, additional measurements were made to assess bulk tissue loss. Statistical analysis was carried out using a two tailed, unequal variance Student T-Test to >95% confidence level.

Results of the analysis are displayed in FIGS. 4 and 5 below.

TABLE 5

Formulations

| Ingredient name | F25 % w/w | F26 % w/w |
|---|---|---|
| Purified water | 31.86251 | 29.3148 |
| Sorbitol, Liquid (Non-crystallizing) | 30 | 30 |
| Silica, Dental Type (Zeodent 153) | 12 | 12 |
| Silica, Dental Type (Zeodent 116) | 6 | 6 |
| Glycerol | 8 | 8 |
| Potassium nitrate | 5 | 5 |
| Polyethylene glycol 300 (PEG-6) | 3 | 3 |
| Cocamidopropyl betaine | 1.2 | 1.2 |
| Flavour | 1.2 | 1.2 |
| Xanthan gum | 0.8 | 0.8 |
| Sodium fluoride | 0.315 | 0.315 |
| Saccharin sodium | 0.35 | 0.35 |

TABLE 5-continued

| | Formulations | |
|---|---|---|
| Ingredient name | F25 % w/w | F26 % w/w |
| Titanium dioxide | 0.1 | 0.1 |
| Sodium hydroxide | 0.07249 | 0.7202 |
| Gantrez | 0.1 | 2 |
| Total | 100 | 100 |

Results

Material Loss [Step Height] Analysis:

The material loss for the treatment groups followed the trend:

[Largest Step] Formulation 26>25≥23≥24>22 [Smallest Step].

The step height advantage for Formulation 22 is statistically significant at a 95% confidence level compared to all other formulations.

Surface Roughness (Sa) Analysis:

The surface roughness for the treatment groups followed the trend:

[Largest Sa] Formulation 26>25≥23≥24>22 [Smallest Sa]

The lower surface roughness of the enamel treated with Formulation 22 is statistically significant at a 95% confidence level compared to all other formulations.

Conclusion

The above data indicate that pre-treatment with the dentifrice containing 0.25% Gantrez (Formulation 22) offers the greatest protection against an erosive challenge. The lowest protection is offered by pretreatment with the dentifrice containing the most Gantrez (2%, Formulation 26).

The invention claimed is:

1. A toothpaste composition comprising sodium fluoride present in an amount of 0.25% by weight of the composition; and 0.25% by weight of the composition of a copolymer of methyl vinyl ether (MVE) with maleic anhydride or acid; wherein the copolymer has a molecular weight in the range of 1,200,000 to 1,500,000; wherein the composition has a slurry pH of about 6.2; and wherein the composition is free of a carboxylic acid or alkali metal salt thereof wherein the carboxylic acid is selected from the group consisting of malonic acid, glutaric acid, tartaric acid, lactic acid and mixtures thereof.

2. A composition according to claim 1 wherein the composition further comprises a pH modifying agent.

3. A composition according to claim 2 wherein the pH modifying agent is sodium hydroxide.

4. A composition according to claim 1 wherein the copolymer is a copolymer of MVE with maleic acid.

5. A composition according to claim 4 wherein the copolymer is a 1:1 copolymer of MVE with maleic acid.

6. A composition according to claim 1 further comprising a desensitising agent.

7. A method of protecting teeth against dental erosion, comprising utilizing the composition according to claim 1.

8. A method of protecting teeth against dental caries, comprising utilizing the composition according to claim 1.

* * * * *